US012649015B2

(12) United States Patent (10) Patent No.: US 12,649,015 B2
Lee et al. (45) Date of Patent: Jun. 9, 2026

(54) EMBOLIZATION HYDROGEL HAVING CONTROLLABLE DEGRADATION TIME, AND PREPARATION METHOD THEREFOR

(71) Applicant: NEXTBIOMEDICAL CO., LTD., Incheon (KR)

(72) Inventors: Don Haeng Lee, Seoul (KR); Eun Hye Lee, Incheon (KR); Yi Xian Li, Incheon (KR); Se Yun Kim, Incheon (KR); Dae Sung Lee, Incheon (KR)

(73) Assignee: NEXTBIOMEDICAL CO., LTD., Incheon (KR)

( * ) Notice: Subject to any disclaimer, the term of this patent is extended or adjusted under 35 U.S.C. 154(b) by 312 days.

(21) Appl. No.: 18/286,725

(22) PCT Filed: Apr. 28, 2022

(86) PCT No.: PCT/KR2022/006131
§ 371 (c)(1),
(2) Date: Oct. 12, 2023

(87) PCT Pub. No.: WO2022/231360
PCT Pub. Date: Nov. 3, 2022

(65) Prior Publication Data
US 2024/0197952 A1 Jun. 20, 2024

(30) Foreign Application Priority Data
Apr. 28, 2021 (KR) ........................ 10-2021-0055086

(51) Int. Cl.
| | | |
|---|---|---|
| *A61L 24/00* | (2006.01) | |
| *A61L 24/04* | (2006.01) | |
| *A61L 24/08* | (2006.01) | |
| *A61L 24/10* | (2006.01) | |

(52) U.S. Cl.
CPC ......... *A61L 24/0031* (2013.01); *A61L 24/046* (2013.01); *A61L 24/08* (2013.01); *A61L 24/102* (2013.01); *A61L 24/104* (2013.01); *A61L 2300/402* (2013.01); *A61L 2300/406* (2013.01); *A61L 2300/44* (2013.01); *A61L 2300/60* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,522,753 | A | 6/1985 | Yannas et al. |
| 2006/0251582 | A1 | 11/2006 | Reb |
| 2010/0081790 | A1 | 4/2010 | Konno et al. |
| 2013/0273162 | A1 | 10/2013 | Li |
| 2014/0079794 | A1 | 3/2014 | Miura et al. |
| 2014/0274945 | A1 | 9/2014 | Blaskovich et al. |
| 2015/0064231 | A1 | 3/2015 | Li |
| 2015/0182658 | A1 | 7/2015 | Rioux et al. |
| 2016/0008508 | A1 | 1/2016 | Nakahara et al. |
| 2016/0228597 | A1 | 8/2016 | Dreher |
| 2022/0023218 | A1* | 1/2022 | Li ........................ A61K 31/704 |

FOREIGN PATENT DOCUMENTS

| | | |
|---|---|---|
| CN | 102585258 A | 7/2012 |
| JP | 5307490 B2 | 10/2013 |
| JP | 2014-58465 A | 4/2014 |
| JP | 2014-58466 A | 4/2014 |
| JP | 2015-512924 A | 4/2015 |
| JP | 5981025 B2 | 8/2016 |
| JP | 2017-508491 A | 3/2017 |
| KR | 10-2008-0018185 A | 2/2008 |
| KR | 10-1575563 B1 | 12/2015 |
| KR | 10-2020-0066574 A | 6/2020 |
| KR | 10-2020-0127964 A | 11/2020 |
| WO | WO 98/03203 A1 | 1/1998 |
| WO | WO2016/093412 A1 | 6/2016 |
| WO | WO 2020/111895 A1 | 6/2020 |

OTHER PUBLICATIONS

International Search Report (PCT/ISA/210) issued in PCT/KR2022/006131, dated Aug. 3, 2022.
Written Opinion of the International Searching Authority (PCT/ISA/237) issued in PCT/KR2022/006131, dated Aug. 3, 2022.
Extended European Search Report for European Application No. 22796192.7, dated May 3, 2024.

* cited by examiner

*Primary Examiner* — Brian Gulledge
(74) *Attorney, Agent, or Firm* — Birch, Stewart, Kolasch & Birch, LLP

(57) ABSTRACT

The present invention relates to: an amorphous of spherical embolisation hydrogel having a degradation time that can be precisely controlled in blood vessels; and a preparation method therefor.

18 Claims, 8 Drawing Sheets

[FIG. 4]

Right : Example 1
Left : Comparative Example 1

EMBOLIZATION HYDROGEL HAVING CONTROLLABLE DEGRADATION TIME, AND PREPARATION METHOD THEREFOR

TECHNICAL FIELD

This application claims the benefit of priority to Korean Patent Application No. 2021-0055086 filed on Apr. 28, 2021, the disclosure of which is incorporated herein by reference in its entirety.

The present invention relates to an embolic hydrogel with adjustable degradation time and a method of preparing the same. More particularly, the present invention relates to an amorphous or spherical embolic hydrogel with precisely adjustable degradation time in a blood vessel and a method of preparing the same.

BACKGROUND ART

Rapid advances in imaging diagnostics have made it possible to pinpoint the location of cancer and a blood vessel that supplies blood to the cancer. This allows for precise delivery of various cancer treatments, such as irradiation, surgical removal, and embolization.

Embolization is a treatment that causes necrosis of a tumor by occluding a blood vessel that supplies blood to the tumor. Transcatheter arterial chemoembolization (TACE) is the most commonly performed treatment for liver cancer. TACE involves a combination of physical embolization of an artery that supplies blood to a tumor and chemical treatment with an anti-cancer drug injected through the artery.

Embolization has been used to treat a variety of other indications, such as uterine fibroids, prostate cancer, lung cancer, and kidney cancer. In recent years, it has been reported that embolization may also be used to treat arthritis and frozen shoulder.

Permanent embolization of a blood vessel reduces effectiveness thereof because the original blood vessel cannot be reopened and a new blood vessel is instead created. In order to treat arthritis, frozen shoulder, etc., it is preferable to perform short-term embolization of a blood vessel that supplies nutrients to a nerve that causes pain. This is because only a nerve cell in an inflamed area must be necrotized with minimal effect on other muscles.

The degradation time of a conventional anticancer embolus is too long, measured in days or weeks, and furthermore, time adjustment is not precise. In order to treat arthritis, frozen shoulder, etc., an embolic agent with more precisely adjustable time is needed. Conventional embolic products include Gelpart, Cali-Gel, and EmboCube, which are amorphous embolic products, and Embosphere, Embozene, and Bead Block, which are spherical embolic products. Each of the conventional embolic products has a long degradation time, and the degradation time thereof cannot be precisely adjusted. Meanwhile, there is a biodegradable embolus, which, however, is amorphous and has a degradation time of two weeks or more, and therefore the biodegradable embolus is not suitable for arthritis or frozen shoulder.

Patent Document 1 is a patent by the applicant of the present invention, which relates to microparticles that can be used as drug-loaded embolic hydrogel microparticles and a method of preparing the same. Patent Document 1 is capable of adjusting the degradation time of an anti-cancer embolic agent when administered in vivo, but the degradation time is in days, like the conventional embolic agent, and therefore Patent Document 1 does not suggest technology capable of adjusting a short time for arthritis or frozen shoulder, etc.

Patent Document 2 relates to gelatin particles having a specific volume swelling rate in the form of a non-porous solid sphere, gelatin particles made by dissolving and retaining a bioactive substance in the gelatin particles, and a device for dispersing the gelatin particles dissolved and impregnated with the bioactive e substance in a syringe with normal saline. Patent Document 2, which has a degradation time in days, does not suggest technology capable of adjusting a short time for arthritis or frozen shoulder, etc., like Patent Document 1.

PATENT DOCUMENTS

Korean Patent Application Publication No. 2020-0066574 ("Patent Document 1")
Japanese Patent Application Publication No. 2014-58466 ("Patent Document 2")

DISCLOSURE

Technical Problem

It is an object of the present invention to provide an embolic hydrogel with adjustable degradation time that can be used for an embolic agent with precisely adjustable degradation time, which is not provided by the conventional embolic agent, and a method of preparing the same. It is another object of the present invention to provide an embolic hydrogel with adjustable degradation time that can be used for an embolic agent with precisely adjustable degradation time and very short degradation time for arthritis or frozen shoulder, etc. and a method of preparing the same.

It is a further object of the present invention to provide an embolic hydrogel having various types of appropriate degradation time for treatment without the use of a cross-linking agent and a method of preparing the same.

Technical Solution

In order to accomplish the above objects, the present invention provides an embolic composition including hydrogel microparticles prepared without using a cross-linking agent. The degradation time in vivo of the hydrogel microparticles according to the present invention is adjusted by heat treatment and/or washing. The washing may be performed using a solvent with a $\delta P$ polar value of 14 or higher.

In particular, the embolic composition according to the present invention may be used for embolization of a joint.

The hydrogel microparticles according to the present invention may be configured such that particles can be produced by thermal denaturation. As a non-limiting example, the hydrogel microparticles may include at least one selected from the biocompatible polymer group consisting of gelatin, collagen, gum, rosin, hyaluronic acid, heparin, dextran, alginic acid, albumin, chitosan, polyglycolide, polylactide, polyhydroxyvalerate, and silk fibroin.

The hydrogel microparticles may be emulsion type microparticles including an organic solvent, and the organic solvent may be at least one selected from the group consisting of methyl acetate, ethyl acetate, propyl acetate, isopropyl acetate, butyl acetate, isobutyl acetate, hexyl acetate, ethyl formate, dimethyl carbonate, diethyl carbonate, 1,3-dioxolidin-2-one, cellulose acetate butyrate, medium chain triglyceride (MCT) oil, vegetable oil, wax, and infused oil. In addition, the emulsion may include no separate emulsifier.

The embolic composition according to the present invention may further include an additional drug, and as a non-limiting example, at least one of a local anesthetic, an antibiotic, and a contrast agent may be added.

In another aspect, the present invention provides a method of preparing hydrogel microparticles prepared through step (a) or step (b):

(a)

1) preparing an aqueous solution of a biocompatible polymer;

2) adding an organic solvent to the aqueous solution of the biocompatible polymer of step 1) so as to be emulsified in order to form micro-sized particles;

3) washing and drying the micro-sized particles prepared in step 2) to obtain micro-sized microparticles;

4) thermally curing the micro-sized microparticles of step 3); and 5) washing, dehydrating, and drying the micro-sized microparticles obtained in step 4); or (b)

1) preparing an aqueous solution of a biocompatible polymer;

2) stirring and/or low-temperature curing the aqueous solution of the biocompatible polymer of step 1) to form a foam and freeze-drying the foam;

3) thermally curing the foamy material of step 2) to obtain micro-sized microparticles;

4) washing and freeze-drying the micro-sized microparticles obtained in step 3); and 5) crushing the foamy material obtained in step 4) to obtain micro-sized microparticles.

The biocompatible polymer may be at least one selected from the group consisting of gelatin, collagen, gum, rosin, hyaluronic acid, heparin, dextran, alginic acid, albumin, chitosan, polyglycolide, polylactide, polyhydroxyvalerate, and silk fibroin, and the organic solvent may be at least one selected from the group consisting of methyl acetate, ethyl propyl acetate, butyl acetate, isobutyl acetate, isopropyl acetate, hexyl acetate, ethyl formate, dimethyl carbonate, diethyl carbonate, 1,3-dioxolidin-2-one, cellulose acetate butyrate, medium chain triglyceride (MCT) oil, vegetable oil, wax, and infused oil.

In addition, cold-curing the micro-sized particles prepared in step 2) at room temperature or lower may be added between step 2) of (a) and step 3) of (a).

In addition, crushing the micro-sized microparticles and sieving the crushed microparticles so as to be divided by particle size may be further added between step 4) of (a) and step 5) of (a) or after step 5) of (a), or sieving the micro-sized microparticles so as to be divided by particle size may be further added after step 5) of (b).

As a non-limiting example, the particle size may be divided into 75 μm to less than 150 μm, 150 μm to less than 350 μm, 350 μm to less than 560 μm, 560 μm to less than 710 μm, 710 μm to less than 1000 μm, 1000 μm to less than 1400 μm, and 1400 μm to less than 2000 μm.

The thermal curing may be performed at 100° ° C. to 200° C. for 10 minutes to 24 hours, and the washing may be performed at a temperature of above 0° ° C. to 40° C. or lower. The washing may be performed using a solvent with a 8P polar value of 14 or higher.

The rate of in vivo degradation of the hydrogel microparticles according to the present invention may be adjusted on an hourly and minute basis by the heat treatment and/or washing.

In addition, the present invention provides hydrogel microparticles prepared using the preparation method and an embolic composition including the microparticles.

In addition, the present invention may provide all possible combinations of the above solving means.

Advantageous Effects

As is apparent from the above description, the present invention is capable of providing embolic hydrogel microparticles with adjustable degradation time that can be used for an embolic agent with precisely adjustable degradation time, which is not provided by the conventional embolic agent, and a method of preparing the same.

(1) The biodegradation time of the hydrogel microparticles according to the present invention can be adjusted to be as short as 30 minutes and as long as 30 days or more.

(2) The biodegradation time of the hydrogel microparticles according to the present invention can be adjusted in units of about 10 minutes.

(3) The hydrogel microparticles according to the present invention are made of a biocompatible polymer and have excellent biological safety.

(4) An embolic agent including the hydrogel microparticles according to the present invention is composed of a biocompatible polymer alone and does not use any chemical crosslinker or additive, and therefore the embolic agent is very safe.

(5) The embolic agent including the hydrogel microparticles according to the present invention can be used as an embolic agent with very short degradation time for arthritis, frozen shoulder, etc.

BEST MODE

Figure 1:
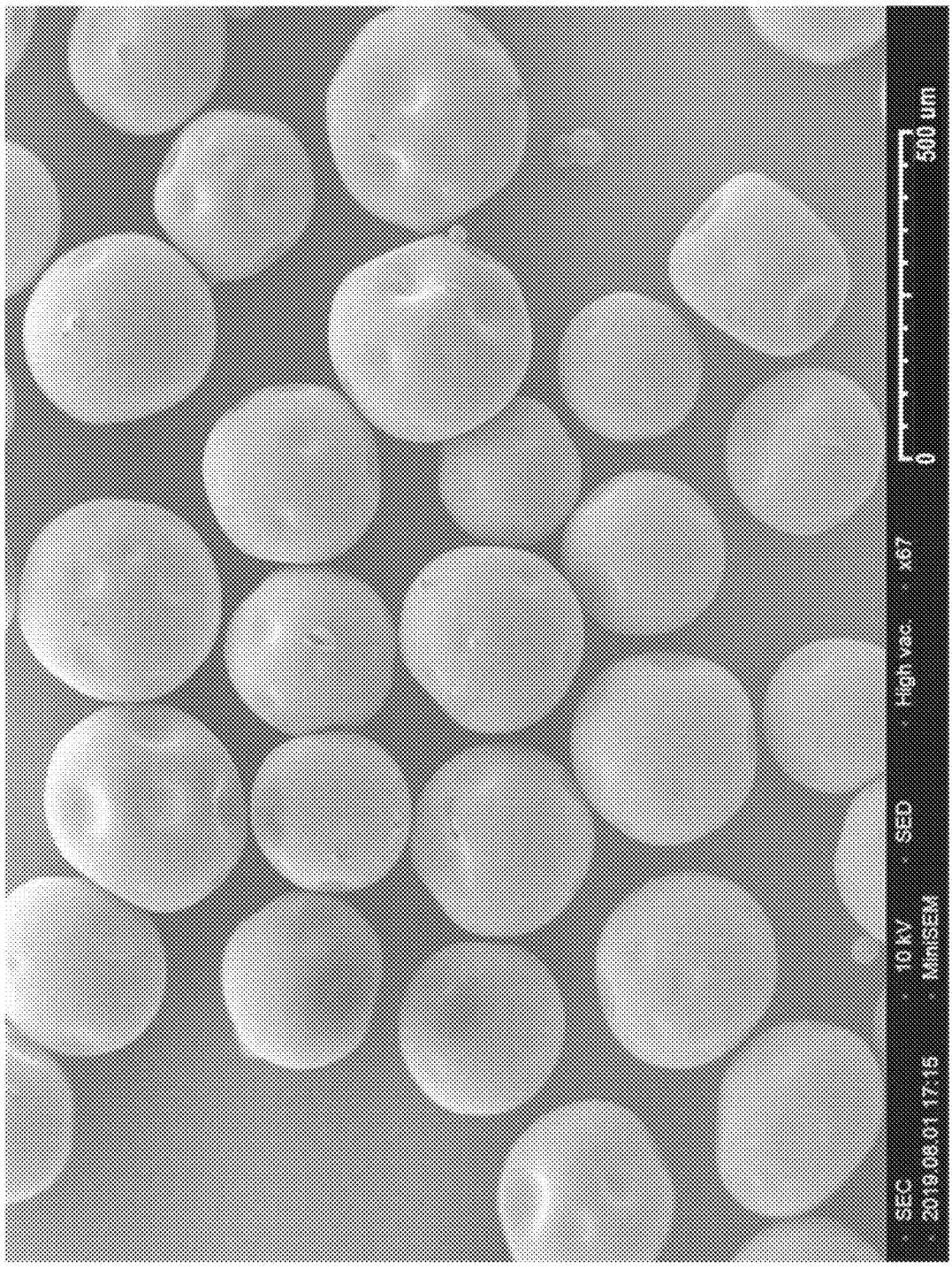
FIG. 1 is a micrograph of spherical hydrogel microparticles according to Example 1 of the present invention. A scale is shown under the micrograph, wherein the total length of gradations is 500 μm.

In the present application, it should be understood that the terms "comprises," "has," "includes," etc., when used in this specification, specify the presence of stated features, numbers, steps, operations, elements, components, or combinations thereof, but do not preclude the presence or addition of one or more other features, numbers, steps, operations, elements, components, or combinations thereof.

It will be understood that, when a component is referred to as being "connected to" or "coupled to" another component, it may be directly connected to or coupled to the other component, or intervening components may be present. In contrast, when a component is referred to as being "directly connected to" or "directly coupled to" another component, there are no intervening components present. Other terms that describe the relationship between components, such as "between" and "directly between" or "adjacent to" and "directly adjacent to", must be interpreted in the same manner.

In addition, unless otherwise defined, all terms, including technical and scientific terms, used in this specification have the same meanings as those commonly understood by a person having ordinary skill in the art to which the present invention pertains. It will be further understood that terms, such as those defined in commonly used dictionaries, should be interpreted as having meanings consistent with their meanings in the context of the relevant art and the present disclosure, and are not to be interpreted in an idealized or overly formal sense unless expressly so defined herein.

Example 1: Preparation of Spherical Hydrogel Microparticles 1) 20 g of gelatin is completely dissolved in 100 ml of 50° C. distilled water.

2) The gelatin solution obtained in step 1) is slowly injected into 400 ml of medium-chain triglyceride (MCT) oil under a stirring condition of 450 rpm to prepare an emulsion.

3) The emulsion prepared in step 2) is cured at 4° C. for 30 minutes, supernatant is removed, the emulsion is washed with acetone, and the emulsion is dried under vacuum.

4) The spherical microparticles obtained in step 3) are thermally treated at 150° C. for 4 hours.

5) The microparticles thermally treated in step 4) are washed with distilled water, are washed with acetone, and are dried under vacuum to obtain final spherical hydrogel microparticles.

Washing Method of Example 1

The washing method is influenced by the ratio of microspheres to a washing solution, washing intensity, and washing time.

50 g of the microspheres according to Example 1 were mixed with 1.5 L of 15° C. distilled water, and stirring was performed at 200 rpm for 30 minutes to wash the microspheres. After 30 minutes, the swollen microspheres were completely settled, supernatant was removed, 1.5 L of 15° C. distilled water was added, and stirring was performed again at 200 rpm for 30 minutes to wash the microspheres. The washing process was performed until the supernatant was completely transparent. In the case of Example 1, washing was performed a total of 3 times.

In the following other examples or comparative example, washing was performed in the same manner as described above.

The washing solution was checked, and it was found that microspheres swelled in solvents with a OP polar value of 14 or higher.

| Solvent | δP polar | Washable |
|---|---|---|
| Acetone | 10.4 | X |
| Ethanol | 8.8 | X |
| Dimethylformamide | 13.7 | X |
| Dimethyl sulfoxide | 16.4 | ◯ |
| Water | 15.1 | ◯ |

Comparative Example 1

Identical to Example 1 except that the last step 5), among the preparation steps of Example 1, was not performed.

Examples 2 to 5: Preparation of Spherical Hydrogel Microparticles

The heat treatment temperature and time in step 4) of Example 1 were changed to 120° C. and 3 hours, respectively. After heat treatment, the microparticles are divided into four parts and washed in distilled water at 4° C. (Example 2), 10° C. (Example 3), 20° C. (Example 4), and 27° C. (Example 5), respectively. After distilled water washing, the microparticles are washed with acetone and dried under vacuum to obtain final spherical hydrogel microparticles.

Examples 6 to 12: Preparation of Spherical Hydrogel Microparticles

The heat treatment temperature and time in step 4) of Example 1 were changed as shown in Table 4 below.

Example 13: Preparation of Amorphous Hydrogel Microparticles 1) 10 g of gelatin is completely dissolved in 100 ml of 50° C. distilled water.

2) The gelatin solution obtained in step 1) is stirred at 14000 rpm for 30 minutes to form enough foam, is cured for 2 hours in a −50° C. environment, and is freeze-dried.

3) The sponge-like gelatin obtained after freeze-drying in step 2) is thermally treated at 150° C. for 5 hours.

4) The sponge-like gelatin thermally treated in step 3) is washed with distilled water, is cured for 2 hours in a −50° C. environment, and is freeze-dried again.

5) The sponge obtained after freeze-drying in step 4) is crushed to obtain final amorphous sponge particles.

Experiment 1: Microscope Observation

Figure 7:
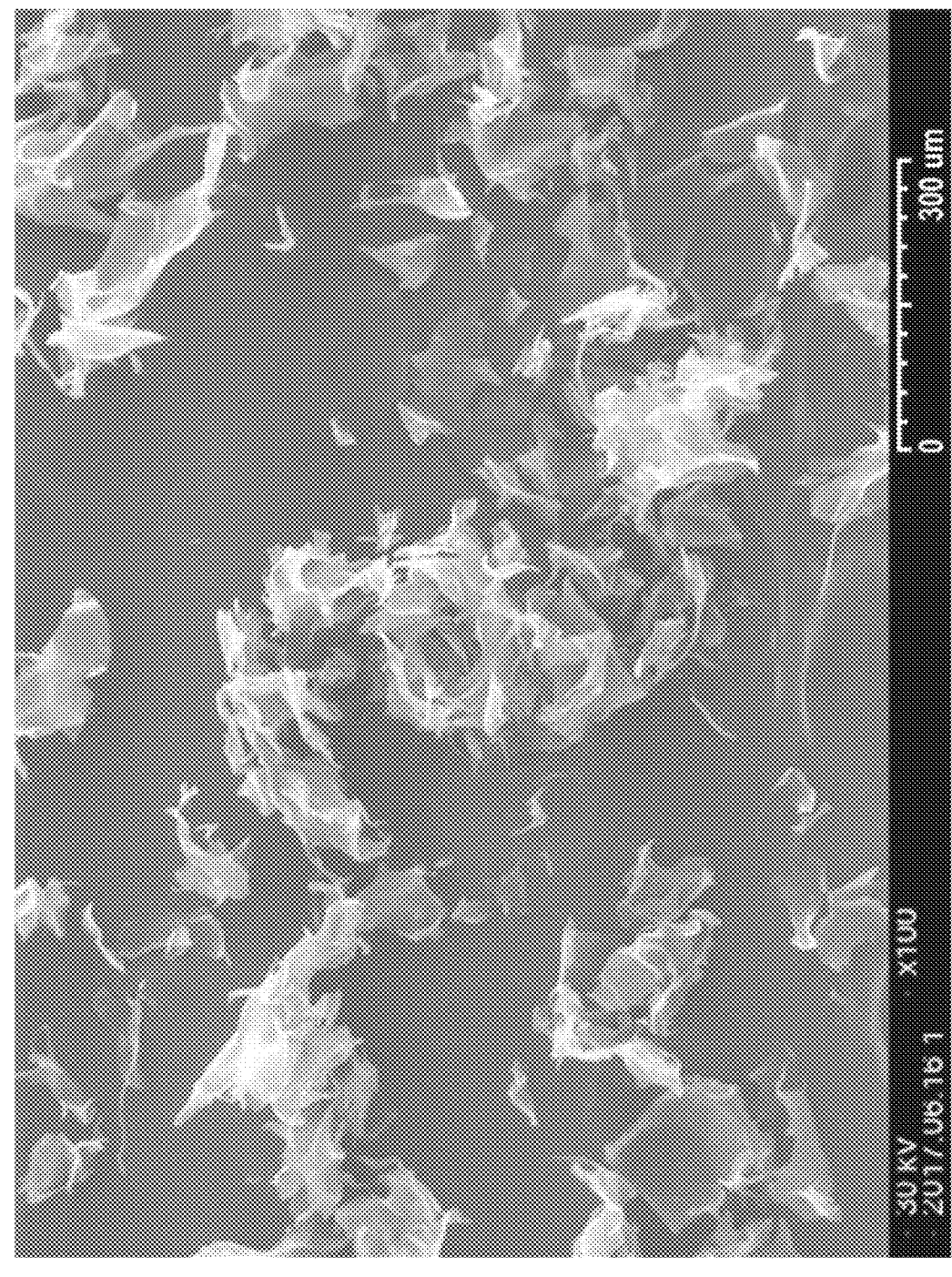
FIG. 7 is a micrograph of amorphous hydrogel microparticles according to Example 13 of the present invention. A scale is shown under the micrograph, wherein the total length of gradations is 300 μm.

The spherical hydrogel microparticles prepared according to Example 1 and the amorphous hydrogel microparticles prepared according to Example 3 were observed using a microscope (see FIGS. 1 and 7, respectively).

Figure 2:
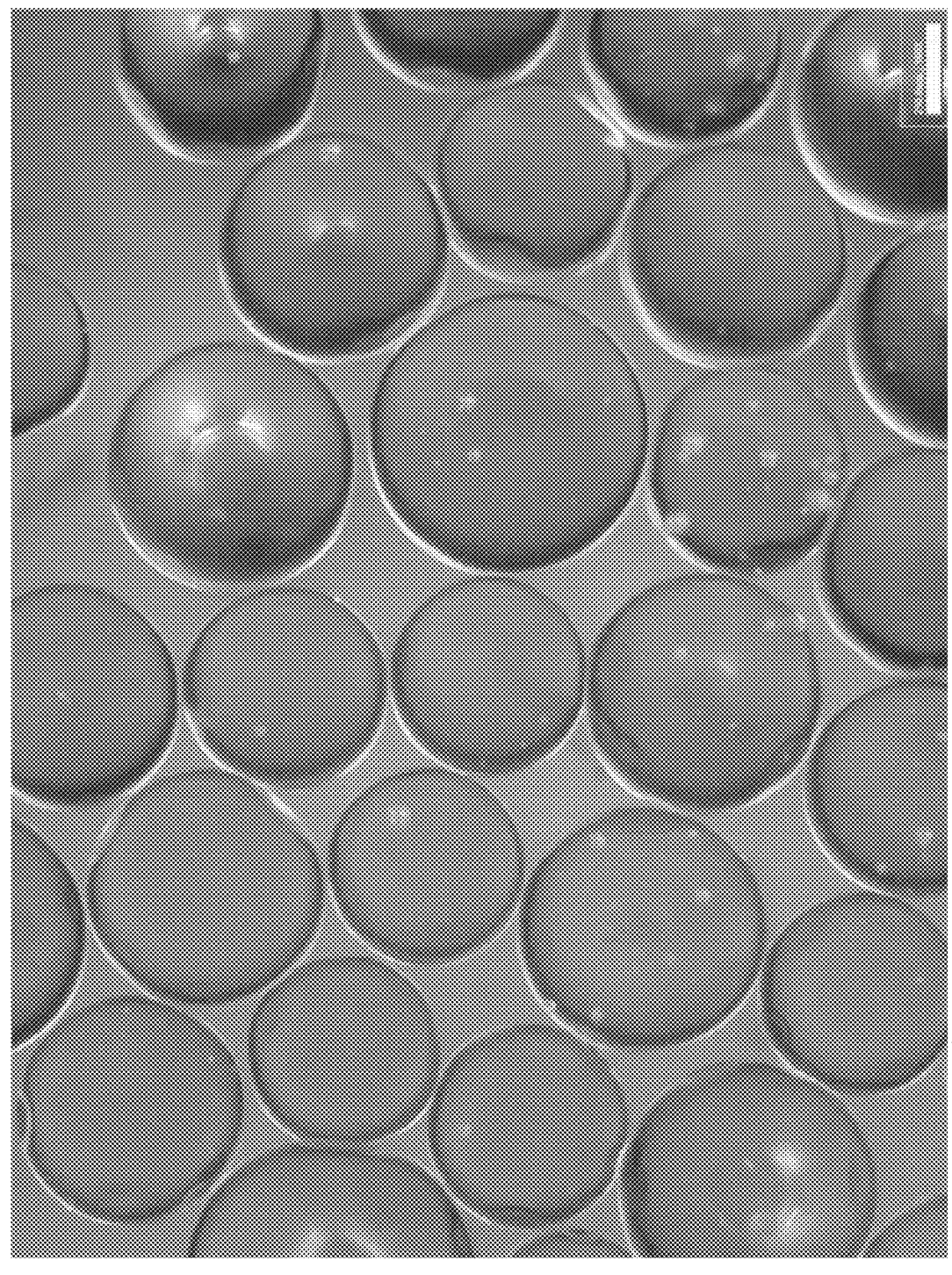
FIG. 2 is a 160× micrograph of the spherical hydrogel microparticles according to Example 1 of the present invention swollen in water. A scale is shown under the right side of the micrograph, wherein the total length of a white bar is 250 μm.
Figure 8:
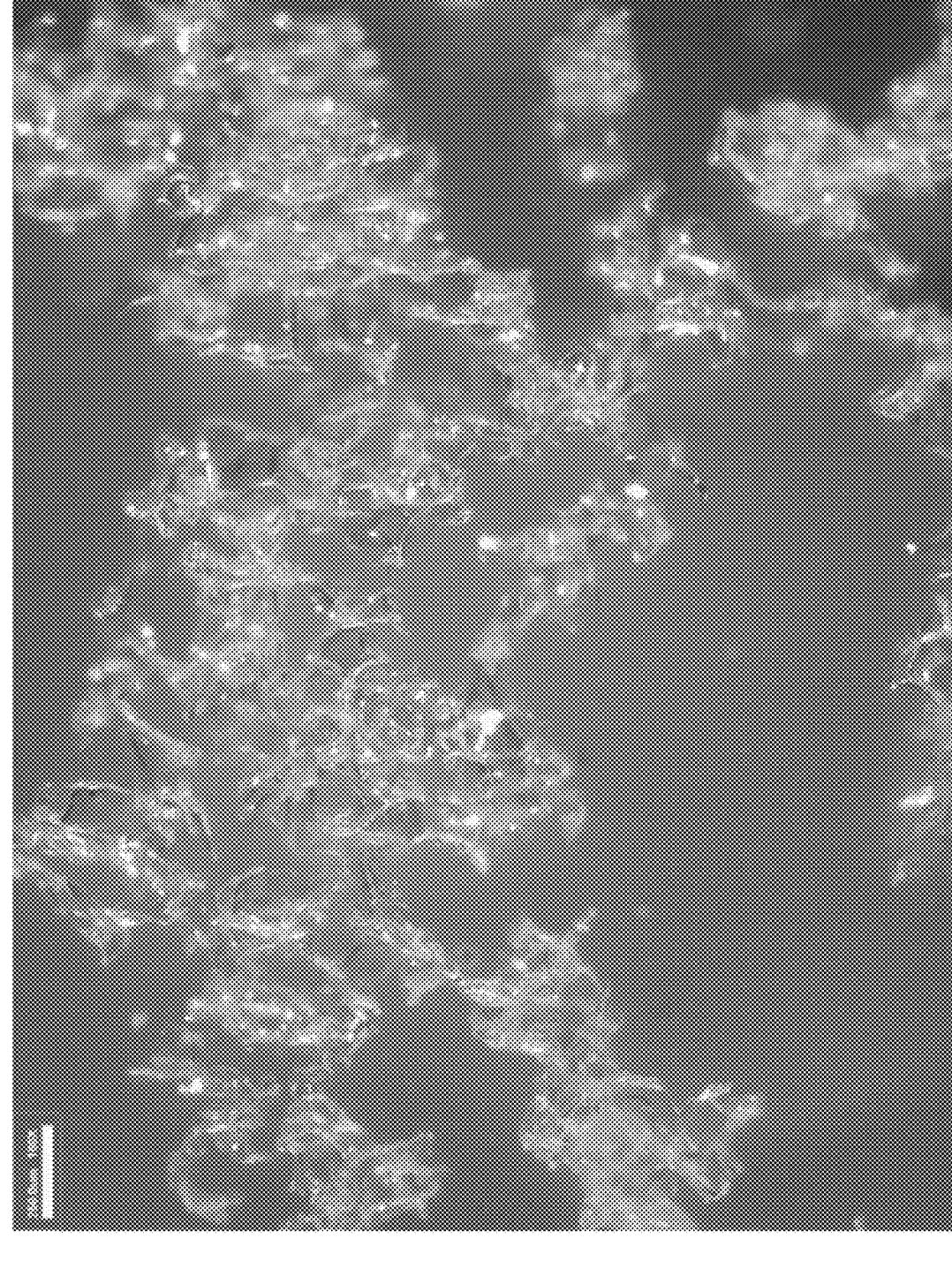
FIG. 8 is a 160× micrograph of the amorphous hydrogel microparticles according to Example 13 of the present invention swollen in water. A scale is shown on the upper left side of the micrograph, wherein the total length of a white bar is 250 μm.

In addition, the spherical hydrogel microparticles prepared according to Example 1 and the amorphous hydrogel microparticles prepared according to Example 13 were immersed in distilled water for 20 minutes to swell, and were observed using the microscope (see FIGS. 2 and 8, respectively).

As can be seen from FIGS. 1 and 2, the hydrogel microparticles prepared according to Example 1 have a spherical shape both before and after swelling.

As can be seen from FIGS. 7 and 8, the amorphous hydrogel microparticles prepared according to Example 13 are amorphous both before and after swelling.

Experiment 2: Measurement of Particle Size Distribution

The particle size distribution of the spherical hydrogel microparticles prepared according to Example 1 was measured using a particle size analyzer.

Figure 3:
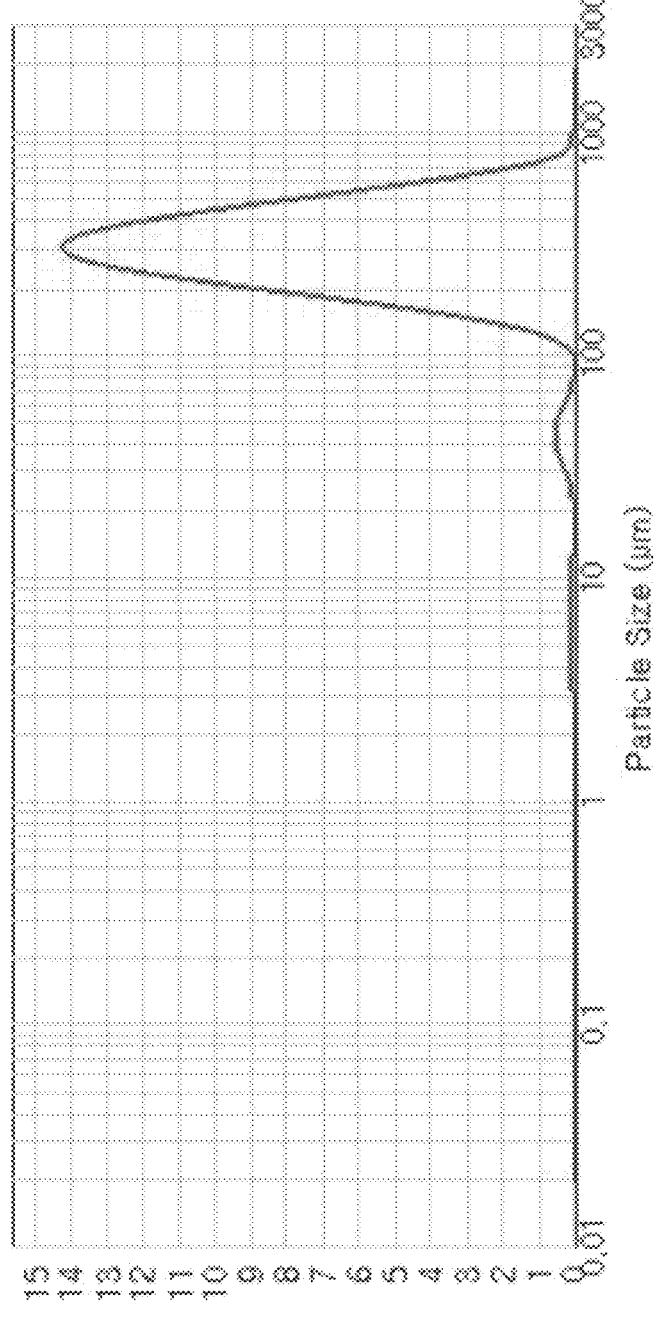
FIG. 3 shows the result of measurement of particle size distribution of the spherical hydrogel microparticles according to Example 1 of the present invention.

FIG. 3 shows the result of measurement of particle size distribution of the spherical hydrogel microparticles according to Example 1 of the present invention. The x-axis is the particle size in μm, and the y-axis is the volume (%) occupied by the particle size.

It can be seen that the spherical hydrogel microparticles according to Example 1 of the present invention have a very narrow degree of particle distribution with an average size of about 300 μm. In addition, the particle size distribution is a desirable size for embolization.

Experiment 3: Elution Test

Eluates were observed for Example 1 and Comparative Example 1.

The elution test was performed by adding 30 ml of a 1×PBS solution to 2 g of microparticles to sufficiently swell the microparticles and eluting the same in a 37° C. shaking water bath for 24 hours.

Figure 4:
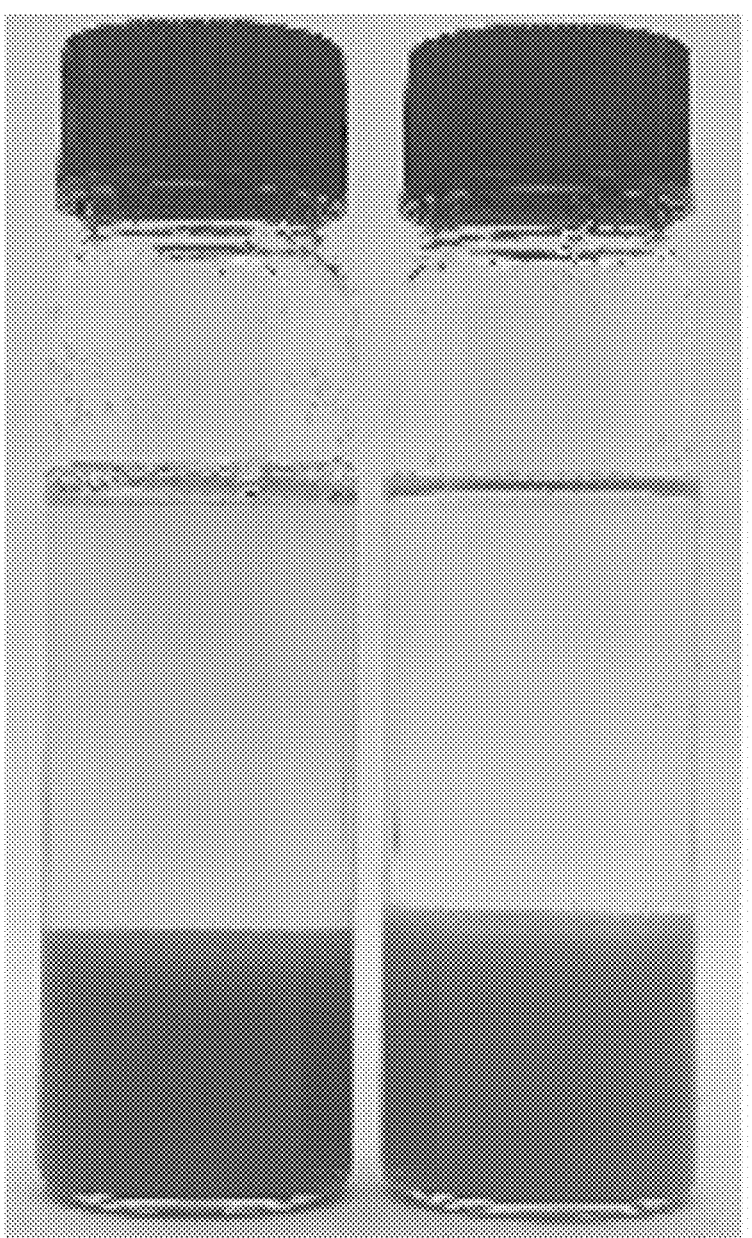
FIG. 4 shows the elution test results of Example 1 and Comparative Example 1.

FIG. 4 shows the elution test results of Example 1 and Comparative Example 1. In FIG. 4, the left side is the result of Comparative Example 1 and the right side is the result of Example 1. It can be seen that Comparative Example 1 has more eluate than Example 1.

Experiment 4: Toxicity Test

A cytotoxicity test (ISO10993-5), an endotoxin test (ISO10993-11), and a pyrogenic test (ISO10993-11) were performed for each of Example 1 and Comparative Example 1.

Figure 5:
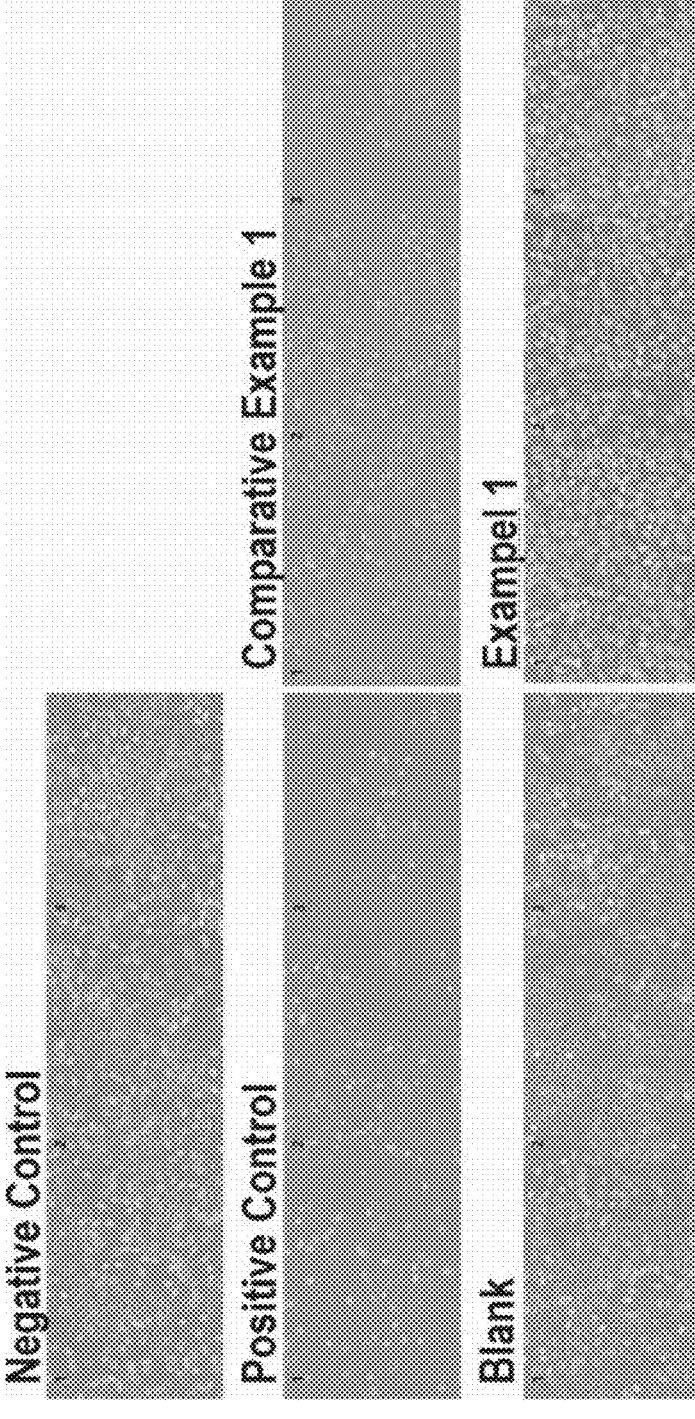
FIG. 5 shows the cytotoxicity test results of Example 1 and Comparative Example 1.

Table 1 and FIG. 5 show the cytotoxicity test results, Table 2 shows the endotoxin test results, and Table 3 shows the pyrogenic test results. Negative Control, Positive Control, and Blank are all based on the above ISO standards.

In Table 1 below, a cell viability of 80% or more is required to pass; in Table 2, an endotoxin value of 20 EU/device or more is required to pass; and in Table 3, if fever of 0.5° C. or more is generated, this is not a pass.

In all three toxicity tests, Comparative Example 1 was a Fail and Example 1 was a Pass.

TABLE 1

| | Cell viability (%) | Morphology |
|---|---|---|
| Negative control | 100.00 | 0 |
| Positive control | 18.07 | 4 |
| Blank | 118.61 | 0 |
| Comparative Example 1 | 10.33 | 1 |
| Example 1 | 81.95 | 2 |

* To pass, cell viability should be more than 80%.

TABLE 2

| | Sample No. | Endotoxin value | Endotoxin Range (50%~200%) | Re-mark |
|---|---|---|---|---|
| Comparative Example 1 | 1 | 10.3 EU/device | 5.2~20.6 EU/device | Fail |
| | 2 | 12.1 EU/device | 6.0~24.2 EU/device | Fail |
| | 3 | 10.2 EU/device | 5.1~20.4 EU/device | Fail |
| Example 1 | 1 | 1.1 EU/device | 0.6~2.3 EU/device | Pass |
| | 2 | 1.5 EU/device | 0.8~3.0 EU/device | Pass |
| | 3 | 1.8 EU/device | 0.9~3.6 EU/device | Pass |

* To pass: 20 EU/device

TABLE 3

| | Comparative Example 1 | | | Example 1 | | |
|---|---|---|---|---|---|---|
| | Rabbit-1 | Rabbit-2 | Rabbit-3 | Rabbit-4 | Rabbit-5 | Rabbit-6 |
| Initial | 39.3 | 39.0 | 39.2 | 39.0 | 39.4 | 39.1 |
| 0 min | 39.3 | 39.3 | 38.9 | 39.1 | 39.4 | 39.0 |
| 30 min | 39.8 | 39.3 | 39.0 | 39.2 | 39.5 | 39.1 |
| 60 min | 40.5 | 39.9 | 39.9 | 39.3 | 39.6 | 39.1 |
| 90 min | 40.8 | 40.4 | 40.6 | 39.3 | 39.6 | 39.2 |
| 120 min | 40.9 | 40.5 | 40.7 | 39.3 | 39.6 | 39.3 |
| 150 min | 41.4 | 40.6 | 40.9 | 39.2 | 39.6 | 39.3 |
| 180 min | 41.4 | 37.8 | 41.0 | 39.2 | 39.6 | 39.2 |
| Max | 2.1 | 1.6 | 1.8 | 0.3 | 0.2 | 0.2 |
| Remark | Fail | Fail | Fail | Pass | Pass | Pass |

* Fail: body temperature rises above 0.5° C.

Experiment 5: Observation of Degradation Time Based on Washing Temperature

Figure 6:
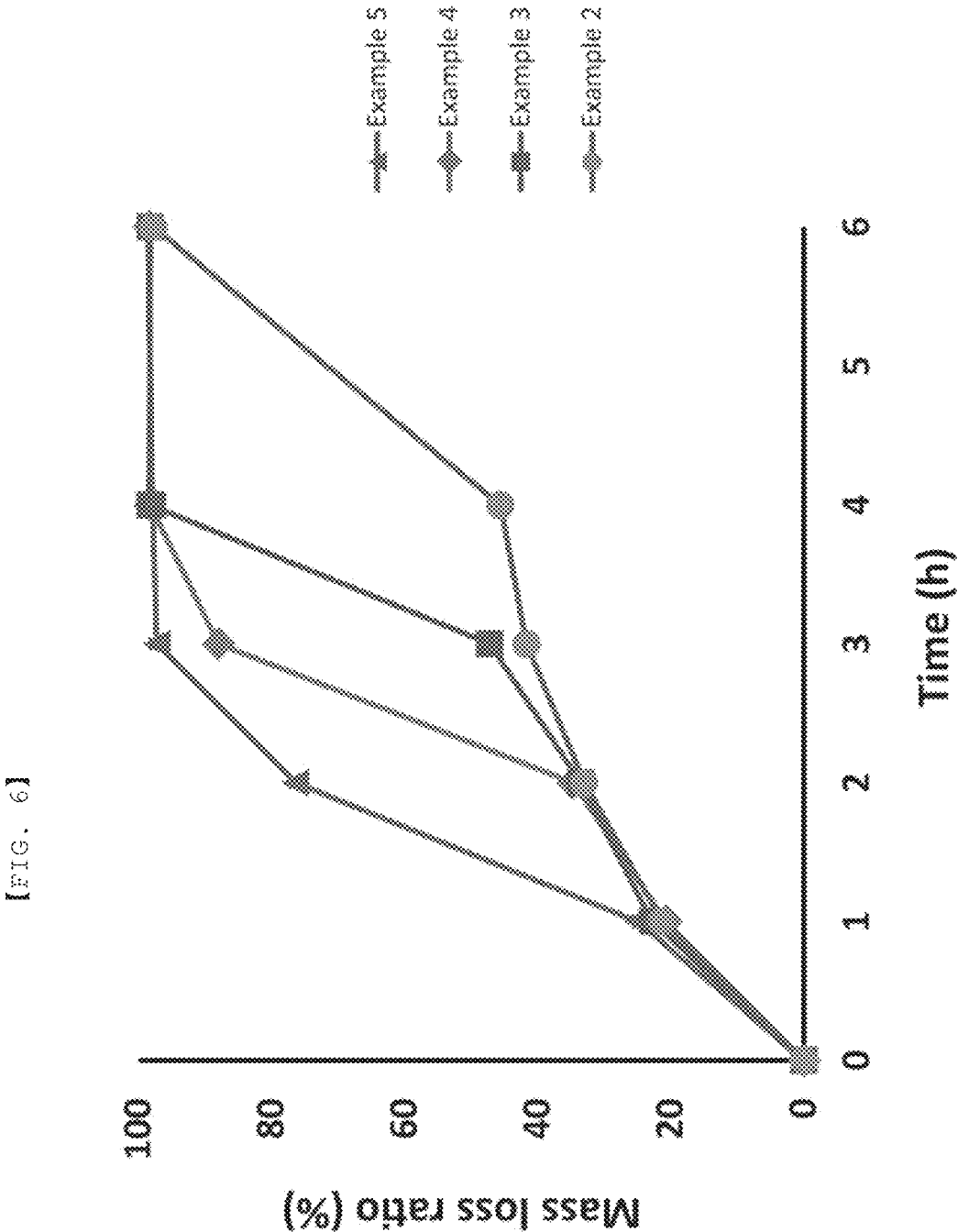
FIG. 6 shows the results of adjusting degradation time using Examples 2 to 5.

The microparticles of Examples 2 to 5 were sieved to collect only microparticles of 100 to 300 μm in size, were introduced into 1× phosphate-buffered saline (PBS), and were observed for degradation time in a constant temperature water bath at 37° C., which is similar to the human body temperature. The results of the degradation time are shown in FIG. 6. As can be seen from Examples 2 to 5, the degradation time can be adjusted at intervals of about 10 minutes by changing only the temperature of the last distilled water washing step in the preparation method according to the present invention. It can also be seen that all of the microparticles according to the present invention can be degraded within a very relatively short time of 1 hour.

Experiment 6: Observation of Degradation Time Based on Heat Treatment Temperature The microparticles of Examples 6 to 12 were sieved to collect only microparticles of 100 to 300 μm in size, were introduced into 1× phosphate-buffered saline (PBS), and were observed for degradation time in a constant temperature water bath at 37° C., which is similar to the human body temperature. The results of the degradation time are shown in Table 4. Experiment 5 shows that the degradation time can be finely adjusted by changing the washing temperature after the same heat treatment. Experiment 6 clearly shows that the degradation time of the microparticles in large units can be adjusted by changing the heat treatment temperature and the heat treatment time.

TABLE 4

| | Heat treatment temperature | Heat treatment time | Degradation time |
|---|---|---|---|
| Example 6 | 110° C. | 24 hours | 5 minutes |
| Example 7 | 120° C. | 3 hours | 1 hour |
| Example 8 | 130° C. | 3 hours | 24 hours |
| Example 9 | 140° C. | 1 hour | 4 hours |
| Example 10 | 140° C. | 2 hours | 40 hours |
| Example 11 | 150° C. | 4 hours | 40 days |
| Example 12 | 200° C. | 10 minutes | 7 days |

It can be seen from Experiments 5 and 6 that, when designing the degradation time of microparticles, it is possible to set the degradation time in large units (days or hours) by adjusting the heat treatment temperature and time first and then to adjust the time in minutes by adjusting the washing temperature.

The invention claimed is:

1. An embolic composition comprising hydrogel microparticles prepared without using a cross-linking agent;
   wherein the hydrogel microparticles are configured such that particles can be produced by thermal denaturation;
   wherein the hydrogel microparticles are swollen by a solvent with a δP polar value of 14 or higher;
   wherein degradation time in vivo of the hydrogel microparticles is adjusted by washing; and
   wherein the washing is performed using a solvent with a δP polar value of 14 or higher.

2. The embolic composition according to claim 1, wherein the hydrogel microparticles comprise at least one selected from a biocompatible polymer group consisting of gelatin, collagen, gum, rosin, hyaluronic acid, heparin, dextran, alginic acid, albumin, chitosan, polyhydroxyvalerate, and silk fibroin.

3. The embolic composition according to claim 1, wherein degradation time in vivo of the hydrogel microparticles is further adjusted by heat treatment.

4. The embolic composition according to claim 1, wherein the hydrogel microparticles are emulsion type microparticles comprising an organic solvent.

5. The embolic composition according to claim 4, wherein the organic solvent is at least one selected from a group consisting of methyl acetate, ethyl acetate, propyl acetate, isopropyl acetate, butyl acetate, isobutyl acetate, hexyl acetate, ethyl formate, dimethyl carbonate, diethyl carbonate, 1,3-dioxolidin-2-one, cellulose acetate butyrate, medium chain triglyceride (MCT) oil, vegetable oil, wax, and infused oil.

6. The embolic composition according to claim 4, wherein the emulsion comprises no separate emulsifier.

7. The embolic composition according to claim 1, wherein at least one of a local anesthetic, an antibiotic, and a contrast agent is added.

8. A method of preparing hydrogel microparticles prepared through step (a) or step (b):
   (a)
   1) Preparing an aqueous solution of a biocompatible polymer;

2) adding an organic solvent to the aqueous solution of the biocompatible polymer of step 1) so as to be emulsified in order to form micro-sized particles;
   3) Washing and drying the micro-sized particles prepared in step 2) to obtain micro-sized microparticles;
   4) Thermally curing the micro-sized microparticles of step 3); and
   5) washing, dehydrating, and drying the micro-sized microparticles obtained in step 4); or
   (b)
   1) Preparing an aqueous solution of a biocompatible polymer;
   2) stirring and/or low-temperature curing the aqueous solution of the biocompatible polymer of step 1) to form a foam and freeze-drying the foam;
   3) Thermally curing the foamy material of step 2) to obtain micro-sized microparticles;
   4) Washing and freeze-drying the micro-sized microparticles obtained in step 3); and
   5) crushing the foamy material obtained in step 4) to obtain micro-sized microparticles.

9. The method according to claim 8, wherein the biocompatible polymer is at least one selected from a group consisting of gelatin, collagen, gum, rosin, hyaluronic acid, heparin, dextran, alginic acid, albumin, chitosan, polyglycolide, polylactide, polyhydroxyvalerate, and silk fibroin.

10. The method according to claim 8, wherein the organic solvent is at least one selected from a group consisting of methyl acetate, ethyl acetate, propyl acetate, isopropyl acetate, butyl acetate, isobutyl acetate, hexyl acetate, ethyl formate, dimethyl carbonate, diethyl carbonate, 1,3-dioxolidin-2-one, cellulose acetate butyrate, medium chain triglyceride (MCT) oil, vegetable oil, wax, and infused oil.

11. The method according to claim 8, wherein cold-curing the micro-sized particles prepared in step 2) at room temperature or lower is added between step 2) of (a) and step 3) of (a).

12. The method according to claim 8, wherein
    crushing the micro-sized microparticles and sieving the crushed microparticles so as to be divided by particle size is further added between step 4) of (a) and step 5) of (a) or after step 5) of (a), or
    sieving the micro-sized microparticles so as to be divided by particle size is further added after step 5) of (b).

13. The method according to claim 8, wherein the thermal curing is performed at 100° C. to 200° C. for 10 minutes to 24 hours.

14. The method according to claim 8, wherein the washing is performed at a temperature of above 0° C. to 40° C. or lower.

15. The method according to claim 8, wherein the washing is performed using a solvent with a δP polar value of 14 or higher.

16. Hydrogel microparticles prepared using the method according to claim 8.

17. An embolic composition comprising the hydrogel microparticles according to claim 16.

18. Hydrogel microparticles prepared using the method according to claim 9.

* * * * *